United States Patent
Cooper

(10) Patent No.: US 9,636,357 B2
(45) Date of Patent: *May 2, 2017

(54) UNIVERSAL HEALING TONIC FOR ARTHRITIS AND PAIN

(71) Applicant: Nathaniel Cooper, Matthews, NC (US)

(72) Inventor: Nathaniel Cooper, Matthews, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 14/602,453

(22) Filed: Jan. 22, 2015

(65) Prior Publication Data

US 2016/0213709 A1    Jul. 28, 2016

(51) Int. Cl.
*A61K 33/00* (2006.01)
*A61K 9/00* (2006.01)
*A61K 31/70* (2006.01)

(52) U.S. Cl.
CPC ............ *A61K 33/00* (2013.01); *A61K 9/0095* (2013.01); *A61K 31/70* (2013.01)

(58) Field of Classification Search
None
See application file for complete search history.

(56) References Cited

PUBLICATIONS

Baking measurements & substitutions—English & Metric ([retrieved from on-line website: http://nationalfestivalofbreads.com/sites/default/files/baking-measurements.pdf, last visit date Sep. 28, 2016]).*

* cited by examiner

*Primary Examiner* — Ernst V Arnold
*Assistant Examiner* — Kyung Sook Chang
(74) *Attorney, Agent, or Firm* — Megan Lyman

(57) ABSTRACT

The present invention relates to a method of consuming a universal potent healing tonic. When consumed according to the method, the arthritic user will experience a large reduction in symptoms, and possible elimination of symptoms altogether, and may also alleviate general pain in the user.

16 Claims, No Drawings

UNIVERSAL HEALING TONIC FOR ARTHRITIS AND PAIN

This invention claims benefit and priority to U.S. patent application Ser. No. 13/948,460 filed Jul. 23, 2013, which claims priority to U.S. Provisional Application No. 61/790,107 filed Mar. 15, 2013 under 35 U.S.C. 119. All benefit to the priority is claimed and is incorporated by reference.

BACKGROUND

Field of Invention

The present invention relates to a method of consuming a universal potent healing tonic. When consumed according to the method, the arthritic user will experience a large reduction in symptoms, and possible elimination of symptoms altogether, and may also alleviate general pain in the user.

Home remedies have been used for hundreds of years to alleviate the many ailments of the human body. Sometimes the best solution can be found right in your kitchen. With the elevated, and sometimes unattainable, cost of traditional health care, many people are turning to home remedies for relief. Moreover, many people prefer to use natural products to synthetic pharmaceuticals traditionally offered by physicians.

Since ancient time natural sugars such as honey, molasses, and maple syrup have been cited as a remedy for a host of ailments. Either alone, or in combination, these products have been linked to curing cancer, heart disease, arthritis, bladder infections, cholesterol, toothaches, colds, upset stomach, gas, influenza, skin infections, indigestions, enhancement of immune system, fatigue, halitosis, assist in weight loss, as well as others. Sodium bicarbonate, otherwise commonly known as baking soda, is similarly extolled for its healing properties.

Mainstream science has confirmed that tumor cells can be killed by increasing the pH in their environment. (Dr. Robert Gillies; Wayne State University School of Medicine: "Acidity generated by the tumor microenvironment drives local invasion": Veronica Estrella, Tingan Chen, Mark Lloyd et al. Cancer Research, Published Online First Jan. 3, 2012; doi: 10.1158/008-5472. CAN-12-2796.) Grants have been given to universities and research institutions to study the effects of pH, including raising pH through sodium bicarbonate, on cancers and arthritis. Still, others believe that raising pH through the use of sodium bicarbonate can eradicate cancer due to the theory that cancer is caused by yeast infection, and the bicarbonate/honey or molasses or syrup combination works to eradicate yeast levels. (Dr. Tullio Simoncini, author of "Cancer is a Fungus").

In combination, sodium bicarbonate and molasses, or maple syrup (hereinafter "natural sugars") have been touted as a cure for many ailments including arthritis, cancer, indigestion, insomnia and many others. Methods and regimens for consuming this combination, however, is something of a mystery. A review of anecdotes and home remedy literature shows a large disparity in recommendations for creating a potent tonic that is safe and effective.

To treat arthritis, physicians like Dr. Parhatsthid Nabadalung from Thailand recommend taking sodium bicarbonate when the urinary pH is below 5.6. Treatment for arthritis, in one person's opinion, is one teaspoon of sodium bicarbonate in 8 ounces of water twice daily.

The average consumer is apt to be confused by the multitude of ingredient combinations, amounts to be used, and frequency of use offered by the present literature. The present method seeks to overcome these hurdles by providing and easy to use system that has resulted in the alleviation of arthritis.

Moreover, the measurement of the correct amounts of the universal potent healing tonic can be viewed as cumbersome. A commercial, user-friendly product could be available to assist the user in consuming the appropriate amount of tonic and is described herein as part of the present invention.

BRIEF SUMMARY OF THE INVENTION

According to one aspect of the invention, the method of consuming the universal potent healing tonic consists of a regimen of consuming sodium bicarbonate and molasses in water over the course of approximately 45 days.

According to another aspect of the present invention, sodium bicarbonate is mixed with approximately 6 ounces of boiling water, then one teaspoon of molasses is immediately added and the mixture is stirred for approximately 30 seconds. The water/bicarbonate mixture is cooled to lukewarm temperature with ice cubes of standard size, and the mixture is consumed.

According to one aspect of the present invention, the method includes consumption of a multivitamin daily, one hour before breakfast.

According to yet another aspect of the present invention, the tonic is prepared and consumed twice daily. The tonic is consumed once before breakfast and one after the final evening meal. This daily rate of consumption is maintained for 15 days (days 1-15).

According to yet another aspect of the present invention, the tonic is then prepared and consumed every evening for 15 more days (days 16 through 30).

According to another aspect of the present invention, the tonic is modified by reducing the sugar and is prepared and consumed once every other day after the evening meal for 15 additional days (days 31-45).

According to another aspect of the present invention, a supplemental preventative dosage may be taken by repeating the dosage of days 31-45.

According to yet another aspect of the invention, the method should be carried out in conjunction with the consumption of at least three 8 oz. glasses of water per day and not exceeding 16, 8 oz. glasses of water.

According to yet another aspect of the invention, a laxative may be taken while performing the method to avoid or alleviate any constipation.

According to yet another aspect of the invention, daily sugar intake should be reduced to not more than approximately 200 grams.

According to one aspect of the present invention, the method should be performed in conjunction with a healthy diet including fruits and vegetables where possible.

According to yet another aspect of the present invention, the method should be performed where the user has a daily intake of sugar not more than approximately 200 grams per day.

According to another aspect of the invention, to assist the user in performing the method, a kit containing 8 ounces of water in a microwave or heat-able material, as well as a pouch containing the appropriate amount of sodium bicarbonate and the appropriate amount of molasses could be packaged and purchased for use by the consumer.

According to yet another aspect of the invention, separate pouches of sodium bicarbonate and molasses in conjunction with a heat-able container containing 8 ounces of water could be packaged for use by a consumer.

According to one aspect of the invention, a container having markings as to the appropriate amount of sodium bicarbonate, molasses and water could be packaged for use by a consumer.

According to yet another aspect of the invention, a container having markings as to the appropriate amount of water as well as a pouch, either separate or together, with the appropriate amount of sodium bicarbonate and molasses could be packaged and provided for use by the consumer.

DETAILED DESCRIPTION

The invention described in detail herein generally relates to a system for producing and consuming a universal potent healing tonic.

A full course of using this healing tonic consists of 45 days. During this time, the user will be taking a multivitamin, such as GERITOL® as in the preferred embodiment, before breakfast. As is apparent to those in the art, other multivitamins can be used. Additionally, the user will consume at least three 8 oz. glasses of water per day, and not exceeding sixteen 8 oz. glasses of water. The user's diet should be considered healthy and include 5 servings per day of fruits and vegetables where possible. A laxative may be taken as needed by the user to avoid or alleviate constipation while executing the course. Moreover, sugar consumption should be limited to not more than 200 grams per day.

Consumption of the healing tonic occurs either before breakfast or in the evening, after the final meal of the day. The tonic is made by preparing 8 ounces of boiling water in one container. In another container, place approximately one tablespoon of sodium bicarbonate, and one teaspoon of GRANDMA'S MOLASSES®. As is apparent, other types of molasses may be substituted. Moreover, other natural sugars may be substituted without departing from the scope of the invention. Next, approximately 6 ounces of boiling water is poured into the container with sodium bicarbonate and stirred to dissolve, then molasses is added, and the mixture is gently stirred for approximately 30 seconds or until the contents are in solution.

Alternatively, 6 ounces of boiling water may be mixed with one tablespoon of sodium bicarbonate and the molasses is added immediately thereafter. The mixture is then gently stirred for approximately 30 seconds.

The mixture is then cooled to lukewarm temperature, approximately 90-100° Fahrenheit. This can be accomplished with the addition of ice (approximately two standard ice cubes having the dimensions of approximately one inch in height, 1 and 2/8 inches in width, and 1 and 3/4 inches in length). Once the mixture is lukewarm, it is consumed.

The mixture is prepared and consumed twice daily, in the morning before breakfast, and in the evening after the last meal, for fifteen consecutive days (days 1-15). Then, the mixture is prepared and consumed every day, in the evening, for the next fifteen days (days 16-30).

Next, the tonic is made by preparing 8 ounces of boiling water in one container. In another container, place approximately one tablespoon of sodium bicarbonate, and one half teaspoon of GRANDMA'S MOLASSES®. As is apparent, other types of molasses may be substituted. Next, approximately 6 ounces of boiling water is poured into the container with sodium bicarbonate, which is dissolved, and then molasses is added, and the mixture is gently stirred for approximately 30 seconds or until the contents are in solution.

Alternatively, 6 ounces of boiling water may be mixed with one tablespoon of sodium bicarbonate and the molasses is added immediately thereafter. The mixture is then gently stirred for approximately 30 seconds.

The mixture is then cooled to lukewarm temperature, approximately 90-100° Fahrenheit. This can be accomplished with the addition of ice (approximately two standard ice cubes). Once the mixture is lukewarm, it is consumed. The mixture is prepared and consumed once every other day, in the evening, for fifteen days (days 31-45). A supplemental preventative sustaining dosage may be taken by repeating the regimen for days 31-45 and consuming the dosage at least once every six months.

Additionally, the mixture may be purchased by the consumer as a kit as is part of the present invention. This kit would include a sealed container of 8 ounces of water. The container is capable of being heated to the boiling temperature of water without degradation. The kit also includes packets of one tablespoon of sodium bicarbonate, one teaspoon, and one half teaspoon of GRANDMA'S MOLASSES®, or other natural sugars, and in sufficient quantities to complete all aspects of the 45 day course of treatment. The packets may be singular (i.e., only sodium bicarbonate), or may have the capability of housing both ingredients without mixing.

Moreover, another embodiment of the kit consisting of a container with markings as to the appropriate amount of water to boil as well as a packets of one tablespoon of sodium bicarbonate, one teaspoon, or one half teaspoon of molasses. The packets may be singular (i.e., only sodium bicarbonate), or may have the capability of housing both ingredients without mixing.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. Accordingly, it should be understood that the embodiments disclosed herein are merely illustrative of the principles of the invention. Various other modifications may be made by those skilled in the art, which will embody the principles of the invention and fall within the spirit and the scope thereof.

I claim:

1. A method for preparing a healing tonic for arthritis and pain comprising:
   a first container comprising 8 ounces of water at approximately 212 degrees Fahrenheit in one container, and a second container comprising approximately 0.5 ounces of sodium bicarbonate and approximately 0.15 ounces of natural sugar;
   combining the contents of said first and second container in a third container adapted to receive the water, sodium bicarbonate, and natural sugar, and mixing until all contents are substantially in solution to create said universal potent healing tonic; and
   wherein said tonic is prepared when it cools to a lukewarm temperature, between approximately 90-100 degrees Fahrenheit, and wherein;
      the tonic is prepared in the morning before a first meal and in the evening after a last meal for a first period of fifteen consecutive days;

after said first period fifteen consecutive days, the tonic is prepared once every day in the evening after said last meal for a second period of fifteen days; and after said second period of fifteen days the tonic is prepared with the same method, but comprising 0.07 ounces of natural sugar, and 0.5 ounces of sodium bicarbonate in 6 ounces of water heated to approximately 212 degrees Fahrenheit, the tonic being prepared once every other evening after said last meal for a third period of fifteen days.

2. The method of claim 1, wherein the natural sugar is molasses.

3. The method of claim 1, wherein the universal potent healing tonic is cooled during preparation to lukewarm temperature rapidly, through the addition of ice.

4. The method of claim 1, wherein after the method of claim 1 is performed, to maintain the alleviation of arthritis;
the tonic is prepared according to the method with 0.07 ounces of natural sugar, 0.5 ounces of sodium bicarbonate and 6 ounces of water heated to approximately 212 degrees Fahrenheit, the tonic is then cooled to a lukewarm temperature, and is prepared every other day after the evening meal.

5. The method of claim 1, wherein a user of the tonic consumes a multivitamin, once daily before the first meal.

6. A method for preparing a healing tonic for arthritis and pain comprising:
adding approximately 0.5 ounces of sodium bicarbonate to approximately 6 ounces of water in a container adapted to receive the water and sodium bicarbonate, wherein the water is at a temperature of approximately 212 degrees Fahrenheit;

adding approximately 0.15 ounces of natural sugar to the sodium bicarbonate and water mixture in the container;

agitating the mixture contained within the container until all contents are in solution to create a universal potent healing tonic; and wherein said tonic is prepared when it cools to a lukewarm temperature, between approximately 90-100 degrees Fahrenheit, wherein;
the tonic is prepared once in the morning before a first meal and again in the evening after a last meal for a period of fifteen consecutive days;

after said first period of fifteen days, the tonic is prepared once every day in the evening after said last meal for a second period of fifteen days; and after said second period of fifteen days the tonic is prepared with the same method, but having 0.07 ounces of natural sugar, and 0.5 ounces of sodium bicarbonate in 6 ounces of water heated to approximately 212 degrees Fahrenheit, cooled to a lukewarm temperature, and being prepared once every other evening after said last meal for a third period of fifteen days.

7. The method of claim 6, wherein the natural sugar is molasses.

8. The method of claim 7, wherein said tonic is cooled to lukewarm temperature rapidly, through the addition of ice.

9. The method of claim 7, to maintain the alleviation of arthritis or pain;

the tonic is prepared according to the method with 0.07 ounces of natural sugar, 0.5 ounces of sodium bicarbonate and 6 ounces of water heated to approximately 212 degrees Fahrenheit, the tonic is then cooled to a lukewarm temperature, and is prepared every other day after the evening meal.

10. The method of claim 7, wherein a user of the tonic consumes a multivitamin, once daily before the first meal.

11. A method for consuming a healing tonic for arthritis and pain comprising:
a sealed container of approximately 6 ounces of water, said container capable of being heated to approximately 212 degrees Fahrenheit without substantial degradation in the container;

a packet containing approximately 0.5 ounces of sodium bicarbonate and a second packet containing approximately 0.15 ounces of natural sugar, wherein said packet and second packet may be in one packet containing separate compartments for said 0.5 ounces of sodium bicarbonate and said 0.15 ounces of natural sugar;

heating the said sealed container with water to approximately 212 degrees Fahrenheit, distributing said packets into said sealed container, mixing said sodium bicarbonate and said natural sugar into solution; and said universal potent healing tonic being fully prepared when it cools to a lukewarm temperature, between approximately 90-100 degrees Fahrenheit, wherein;
the universal potent healing tonic is prepared once in the morning before a first meal and again in the evening after a last meal for a period of fifteen consecutive days;

after said first period fifteen days the tonic is prepared once every day in the evening for a second period of fifteen days; and after said second period of fifteen days the tonic is prepared with the same method, but having 0.07 ounces of sugar, and 0.5 ounces of sodium bicarbonate in 6 ounces of water heated to 212 degrees Fahrenheit and cooled to a lukewarm temperature, being prepared once every other evening after said last meal for a third period of fifteen days.

12. The method of claim 11, wherein the natural sugar is molasses.

13. The method of claim 11, wherein the tonic is cooled to lukewarm temperature rapidly, through the addition of ice.

14. The method of claim 13, to maintain the alleviation of arthritis or pain;
the tonic is prepared according to the method with 0.07 ounces of natural sugar, 0.5 ounces of sodium bicarbonate and 6 ounces of water heated to approximately 212 degrees Fahrenheit, the tonic is then cooled to a lukewarm temperature, and is prepared every other day after the evening meal.

15. The method of claim 13, wherein the amount of sodium bicarbonate 0.25 ounces.

16. The method of claim 13, wherein a user of the tonic consumes a multivitamin, once daily before the first meal.

* * * * *

UNITED STATES PATENT AND TRADEMARK OFFICE
CERTIFICATE OF CORRECTION

PATENT NO.        : 9,636,357 B2
APPLICATION NO.   : 14/602453
DATED             : May 2, 2017
INVENTOR(S)       : Cooper Page 1 of 1

It is certified that error appears in the above-identified patent and that said Letters Patent is hereby corrected as shown below:

On the Title Page

Item (54) Title, should read:
--Universal Healing Tonic for Arthritis, Cancer and Pain--

Signed and Sealed this
Thirty-first Day of July, 2018

Andrei Iancu
*Director of the United States Patent and Trademark Office*